United States Patent [19]

DaVanzo et al.

[11] Patent Number: 5,194,426
[45] Date of Patent: Mar. 16, 1993

[54] METHOD FOR NERVE GROWTH INDUCTION

[75] Inventors: John P. DaVanzo, Greenville; Joseph W. Paul, Jr., Ayden, both of N.C.

[73] Assignee: East Carolina University, Greenville, N.C.

[21] Appl. No.: 681,310

[22] Filed: Apr. 8, 1991

Related U.S. Application Data

[62] Division of Ser. No. 253,167, Oct. 4, 1988, Pat. No. 5,023,238.

[51] Int. Cl.$^5$ .................. A61K 37/02; A61K 37/36
[52] U.S. Cl. ............................ 514/21; 514/12; 514/2; 514/526; 530/350; 530/839; 530/848; 530/854
[58] Field of Search .............. 514/2, 12, 21, 526, 514/519; 530/350, 839, 848, 854

[56] References Cited

U.S. PATENT DOCUMENTS

| | | |
|---|---|---|
| 2,719,861 | 10/1955 | Carboni . |
| 3,311,539 | 3/1967 | Eberts . |
| 5,023,238 | 6/1991 | DaVanzo .............................. 514/21 |

OTHER PUBLICATIONS

F. Hefti and W. J. Weiner, Annals of Neurology, 20, 275 (1986).
K. L. Davis and R. C. Mohs, The New England Journal of Medicine, 315, 1286 (1986).
S. H. Appel, Annals of Neurology, 10, 499 (1981).
S. Varon, et al., Biochemistry, 6, 2202 (1967).
R. T. Houlihan and J. P. DaVanzo, Experimental Neurology, 10, 183 (1964).
L. A. Green and E. M. Shooter, Ann. Rev. Neurosci., 3, 353 (1980).
B. A. Yankner and E. M. Shooter, Ann. Rev. Biochem., 51, 845 (1985).
S. Haleous and J. Patrick, Cell, 22, 571 (1980).
B. K. Schrier, et al., The Pharmacologist, 30, 128.2 (1988).
J. P. DaVanzo, et al., The Pharmacologist, 30, 59.9 (1988).
J. P. DaVanzo, et al., The Pharmacologist, 30, 128.2 (1988).
J. W. Paul and J. P. DaVanzo, Society of Neuroscience, 346.10, Oct. 29-Nov. 3, 1989.
B. K. Schrier and L. Shuster, J. Neurochemistry, 14, 977 (1967).
T. Nagatsu, et al., Analyt. Biochem., 9, 122 (1964).
J. P. DaVanzo, et al., Archive Int. Pharmacodyn., 41, 299 (1963).
H. Gnahn, et al., Developmental Brain Research, 9, 45, (1983).

*Primary Examiner*—F. T. Moezie
*Attorney, Agent, or Firm*—Raymond R. Wittekind

[57] ABSTRACT

A composition comprising nerve growth factor and 2-amino-1,1,3-tricyano-1-propene useful for the induction, stimulation, and maintenance of nerve growth, and methods of potentiating choline O-acetyltransferase and tyrosine hydroxylase by 2-amino-1,1,3-tricyano-1-propene are disclosed.

11 Claims, No Drawings

METHOD FOR NERVE GROWTH INDUCTION

This is a division of application Ser. No. 253,167 filed Oct. 4, 1988, now U.S. Pat. No. 5,023,238.

INTRODUCTION

The present invention relates to nerve growth induction, stimulation, and maintenance, and enzyme potentiation. More particularly, the present invention relates to a composition comprising nerve growth factor and 2-amino-1,1,3-tricyano-1-propene and a method of inducing, stimulating, and maintaining nerve growth therewith, and methods of potentiating choline-O-acetyltransferase and tyrosine hydroxylase by means of 2-amino-1,1,3-tricyano-1-propene.

BACKGROUND OF THE INVENTION

Nerve growth plays a major role in the development of host nervous systems, as well as the survival and regeneration of component nerve cells subject to damage or destruction by injury or disease, such as cognitive disorders associated with dementia.

Nerve growth factor, a polypeptide, induces nerve growth in hosts (for reviews on nerve growth factor, see L. A. Green and E. M. Shooter, Ann. Rev. Neurosci., 3, 353 (1980) and B. A. Yanker and E. M. Shooter, Ann. Rev. Biochem., 51, 845 (1982)). 2-Amino-1,1,3-tricyano-1-propene, a dimer of malnonitrile, also promotes nerve growth in host systems (see, for example, R. T. Houlihan and J. P. DaVanzo, Experimental Neurology, 10, 183 (1964). It has now been found that nerve growth factor in combination with 2-amino-1,1,3-tricyano-1-propene synergistically induces, stimulates, and maintains nerve growth, thereby rendering the combination more effective than either component in restoring nerve function diminished by injuries or degenerative conditions, e.g., Alzheimer's disease (see F. Hefti and W. J. Weiner, Annals of Neurology, 20, 275 (1986).

Cholinergic and adrenergic defects are also implicated in nerve degenerative disorders (see, for example, K. L. Davis and R. C. Mohs, The New England Journal of Medicine, 315, 1286 (1986). It has now also been found that 2-amino-1,1,3-tricyano-1-propene potentiates choline-O-acetyltransferse and tyrosine hydroxylase, thereby augmenting its nerve growth restorative properties and usefulness in nerve degenerative conditions including, e.g., Parkinson's disease, S. H. Appel, Ann. Neurol., 10, 499 (1981).

DESCRIPTION OF THE INVENTION

The present invention relates to a composition comprising nerve growth factor and 2-amino-1,1,3-tricyano-1-propene useful for the induction, stimulation, and maintenance of nerve growth in hosts. The present invention also relates to the potentiation of choline-O-acetyltransferase and tyrosine hydroxylase by 2-amino-1,1,3-tricyano-1-propene.

As used throughout the specification and appended claims, the phase "inducing nerve growth" refers to the production of nerve cells from non-neuritic cells; the phrase "stimulating nerve growth" refers to the enhanced production of nerve cells from neuritic cells; the phrase "maintaining nerve growth" refers to the protection or continuing existence of nerve cells; the term "potentiating" refers to the enhancement of the effects of an agent by another agent so that the total effect is greater than the sum of the effects of either agent; the expression "cholinergic nerves" refers to nerves which liberate acetylcholine at a synapse; and the expression "adrenergic nerves" refers to nerves which liberate catecholamines.

2-Amino-1,1,3-tricyano-1-propene is prepared by the methods described in U.S. Pat. No. 2,719,861, issued Oct. 4, 1955.

Nerve growth factor is isolated by the processes reported in S. Varon, et al., Biochem., 6, 2202 (1967). Included among nerve growth factors are those derived from fish, reptiles, avaian species, and mammals such as mice and rabbits. The male mouse submaxillary gland is a particularly abundant source of nerve growth factor.

Administration of a composition of nerve growth factor and 2-amino-1,1,3-tricyano-1-propene to a host, a mammal, for example, a mouse or a rabbit induces, stimulates, and maintains nerve growth within nervous systems. Among nervous systems there may be mentioned the central, peripheral, and autonomic nervous systems. Representative nerves of the central nervous systems are cholinergic and adrenergic nerves; representative nerves of the peripheral nervous system are the sciatic, ulnar, radials, and median nerves; and representative nerves of the autonamic nervous system are the vagus, facial, glosso-pharyngeal, and spanchnic nerves.

The nerve growth induction, stimulation, and maintenance effects of the composition of nerve growth factor and 2-amino-1,1,3-tricyano-1-propene are demonstrated as follows:

Rat adrenal pheochromcytoma (PC-12) cells (commercially available and on deposit in the American Type Culture Collection (Deposit No. ATCC CRL 1721)) are maintained in Dulbecco's modified eagles media-high glucose (DMEM-H) with 5% fetal calf serum and 5% horse serum. PC-12 cells ($5 \times 10^5$), counted by means of a hemacytometer, are plated in 25 mls of (DMEM-H) in 75 cm$^2$ untreated plastic flasks (Costar) and kept in an atmosphere of 7.5% carbon dioxide at 37° C. PC-12 cells are fed every 3-4 days by decantation of the media and the addition of fresh media, and the cultures are split every week. PC-12 cells ($1-5 \times 10^5$ cells per well) are plated in 96-well tissue culture plates and diluted in concentrations of nerve growth factor, 2-amino-1,1,3-tricyano-1-propene, 2-amino-1,1,3-tricyano-1-propene and nerve growth factor, and media without additives. Neutrite outgrowth was determined, after 24, 48, and 72 hours, by counting the percentage of cells with neurites that are twice the cell body length relative to the total number of cells. Potentiation and synergism experiments are carried out with constant concentrations of 2-amino-1,1,3-tricyano-1-propene and various nerve growth factor concentrations over a range of 0.1 ng/ml to 100 ng/ml (subthreshold to maximum). Neurite outgrowth is determined as above.

RESULTS

| Compound or Composition | Peak Conc | Count (% of cells) |
|---|---|---|
| nerve growth factor | 50 ng/ml @ 48 hr | 50 |

-continued

| Compound or Composition | RESULTS Peak Conc | | Count (% of cells) |
|---|---|---|---|
| 2-amino-1,1,3-tricyano-1-propene | 20 ug/ml @ 48 hr | | 27 |
| nerve growth factor | 0.1 ng/ml @ 48 hr | | 3.0 |
| 2-amino-1,1,3-tricyano-1-propene | 132 pg/ml @ 48 hr | | 3.0 |
| nerve growth factor and 2-amino-1,1,3-tricyano-1-propene | @ 0.1 ng/ml @ 132 pg/ml | @ 48 hr | 54 |
| nerve growth factor and 2-amino-1,1,3-tricyano 1-propene | @ 0.1 ng/ml @ 20 ug/ml | @ 48 hr | 50 |
| Control | | | 3.0 |

Nerve growth induction, stimulation, and maintenance are achieved when the compositions are administered to a subject requiring such treatment as an effective oral, parenteral, intracerebral, or intravenous dose of from about 15 to about 45 $\mu$g/kg of body weight per day. A particularly preferred effective amount is about 20 $\mu$g/kg of body weight per day. It is to be understood, however, that for any particular subject, specific dosage regimens should be adjusted to the individual need and the professional judgment of the person administering or supervising the administration of the aforesaid compositions. It is to be further understood that the dosages set forth herein are exemplary only and they do not, to any extent, limit the scope or practice of the invention.

Administration of 2-amino-1,1,3-tricyano-1-propene to a host, a mammal, for example, a mouse, or a rabbit, potentiates the effects of choline O-acetyltransferase and tyrosine hydroxylase. The potentiation of the effects of choline-O-acetyltransferase is demonstrated as follows:

Rat adrenal pheochromocytoma (PC-12) cells ($1 \times 10^5$ per well) are plated on collagen treated 24 well plates (Costar) in dilutions of nerve growth factor, 2-amino-1,1,3-tricyano-1-propene, 2-amino-1,1,3-tricyano-1-propene and nerve growth factor, and media without additives for 4 days, and choline-O-acetyl transferase activity is measured by the method of B. K. Schrier and L. Shuster, J. Neurochem., 14, 977 (1967). Briefly, after incubation media is removed from the plated cells and the wells are washed three times with phosphate buffer. Cells are lysed with a solution of triton X-100 and 1uCi of $^{14}$C-acetyl coenzyme is added to each well. The plates are then incubated at 37° C. for 1 hour and stopped with the addition to each well of 1 ml of cold water. The fluid in each well is poured over an anion exchange column, the effluent is counted by addition of Scinti-Verse E, and the activity is determined by measuring radioactivity on a scintillation counter.

| | RESULTS | |
|---|---|---|
| Compound | Conc | Rate of Formation of Acetylcholine |
| 2-amino-1,1,3-tricyano-1-propene | 132 pg/ml | 11.8 ± 1.6 pmol/hr/$\mu$g of total protein |
| Control | | 7.4 ± 0.64 pmol/hr/$\mu$g of total protein |

The potentiation of the effects of tyrosine hydroxylase is demonstrated as follows:

Rat adrenal pheochromocytoma (PC-12) cells ($1 \times 10^6$ cells) are plated in collagen treated 60 mm petri dishes in dilutions of nerve growth factor, 2-amino-1,1,3-tricyano-1-propene, nerve growth factor plus 2-amino-1,1,3-tricyano-1-propene, and media without additives, and incubated at 37° C. for 1 hour. Tyrosine hydroxylase activity is measured by the method of Nagatsu, et al., Analyt. Biochem., 9, 122 (1964) with minor modifications. Briefly, after incubation, the plates are washed three times in phosphate buffer, scraped into 400 ul of tris acetate buffer, and frozen until assayed. For the assay, the cells are thawed, homogenized, and centrifuged. Supernatant (50 ul) is assayed for tyrosine hydroxylase activity by addition of 0.5 uCi of $^3$H-tyrosine in 50 ul of buffer, and incubation of the mixture at 37° C. for thirty minutes. The reaction is terminated by addition of 200 ul of acetic acid, and activity is determined by scintillation counting of tritiated water contained in the effluent of the sample after treatment on an anion exchange column.

| | RESULTS | |
|---|---|---|
| Compound | Conc | Rate of Formation of $^3$H$_2$O |
| 2-amino-1,1,3-tricyano-1-propene | 132 pg/ml | 12.78 ± 0.97 fmol/hr/$\mu$g of total protein |
| Control | | 6.25 ± 0.68 fmol/hr/$\mu$g of total protein |

Choline O-acetyltransferase and tyrosine hydroxylase potentiation is achieved when the compound is administered to a subject requiring such treatment as an effective oral, parenteral, intracerebral, or intravenous dose of from about 15 to about 45 $\mu$g/kg of body weight per day. A particularly prefered effective amount is about 20 $\mu$g/kg of body weight per day. It is to be understood, however, that for any particular subject, specific dosage regimens should be adjusted to the individual need and the professional judgment of the person administering or supervising the administration of the aforesaid compounds. It is to be further understood that the dosages set forth herein are exemplary only and they do not, to any extent, limit the scope or practice of the invention.

Effective amounts of the compound and compositions may be administered to a subject by any one of various methods, for example, orally as in capsules or tablets, or intracerebrally, intravenously, or parenterally in the form of sterile solutions. The compound or compositions, while effective themselves, may be formulated and administered in the form of their pharmaceutically acceptable addition salts for purposes of stability, convenience of crystallization, increased solubility and the like.

The compound and compositions may be administered orally, for example, with an inert diluent or with an edible carrier. They may be enclosed in gelatin capsules or compressed into tablets. For the purpose of oral therapeutic administration, the aforesaid compound and compositions may be incorporated with excipients and used in the form of tablets, troches, capsules, elixirs, suspensions, syrups, wafers, chewing gums, and the like. These preparations should contain at least 0.5% of active compound, but may be varied depending upon the particular form and may convenienctly be between 4.0% to about 70% of the weight of the unit. The amount of compound and compositions in such composition is such that a suitable dosage will be obtained. Prefered compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; and excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compound or compositions, sucrose as a sweetening agent and certain preservatives, dyes, colorings, and flavors. Materials used in preparing these various compositions should be pharmaceutically pure and non-toxic in the amounts used.

For the purpose of parenteral, intravenous, or intracerebral therapeutic administration, compound and compositions may be incorporated into a solution or suspension. These preparations should contain at least 0.1% of the aforesaid compound or compositions, but may be varied between 0.5% and about 50% of the weight thereof. The amount of active compound or composition in such compositions is such that a suitable dosage will be obtained. Prefered compositions and preparations according to the present invention are prepared so that a parenteral, intravenous, or intracerebral dosage unit contains between 0.5 to 100 mgs of the active compound or composition.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral, intravenous, or intracerebral preparation can be enclosed in ampoules, disposable syringes or multiple dose vials made of glass or plastic.

We claim:

1. A method of inducing nerve growth in a host requiring nerve growth induction comprising administering a nerve growth inducing effective amount of a composition consisting essentially of nerve growth factor and 2-amino-1,1,3-tricyano-1-propene.

2. A method according to claim 1 wherein the effective amount of the composition is between about 15 $\mu g/kg$ of body weight and about 45 $\mu g/kg$ of body weight.

3. The method according to claim 2 wherein the effective amount of the compound is about 20 $\mu g/kg$ of body weight.

4. A method according to claim 1 wherein the nerve is part of the central nervous system.

5. A method according to claim 1 wherein the nerve is part of the peripheral nervous system.

6. A method according to claim 1 wherein the nerve is part of the autonomic nervous system.

7. The method according to claim 4 wherein the nerve of the central nervous system is selected from the group consisting of cholinergic and adrenergic nerves.

8. The method according to claim 5 wherein the nerve of the peripheral nervous system is selected from the group consisting of the sciatic, ulnar, radial, and median nerves.

9. The method according to claim 6 wherein the nerve of the autonomic nervous system is selected from the group consisting of the vagus, facial, glosso-pharyngeal, and splanchnic nerves.

10. The method according to claim 1 wherein nerve growth refers to the bulk of the nerve.

11. The method according to claim 1 wherein nerve growth refers to the extension of the nerve.

* * * * *